United States Patent
Grouzmann et al.

(10) Patent No.: US 6,337,069 B1
(45) Date of Patent: Jan. 8, 2002

(54) METHOD OF TREATING RHINITIS OR SINUSITIS BY INTRANASALLY ADMINISTERING A PEPTIDASE

(75) Inventors: Eric Grouzmann, La Conversion; Jean-Silvain Lacroix, Geneva; Michel Monod, Lausanne, all of (CH)

(73) Assignee: B.M.R.A. Corporation B.V., Rotterdam (NL)

( * ) Notice: Subject to any disclaimer, the term of this patent is extended or adjusted under 35 U.S.C. 154(b) by 0 days.

(21) Appl. No.: 09/794,236

(22) Filed: Feb. 28, 2001

(51) Int. Cl.$^7$ .............................. C12N 9/48; C12N 9/50; A61K 38/48; A61K 9/14
(52) U.S. Cl. ..................... 424/94.63; 435/212; 435/219; 424/489
(58) Field of Search .......................... 424/94.63, 94.64, 424/489; 435/212, 219

(56) References Cited

PUBLICATIONS

Abbott, et al., "Cloning, Expression and Chromosomal Localization of a Novel Human Dipeptidyl Peptidase (DPP) IV Homolog, DPP8," *Eur. J. Biochem* 267:6140–6150 (2000).

Abbott, et al., "Genomic Organization, Exact Localization, and Tissue Expression of the Human CD26 (Depeptidyl Peptidase IV) Gene," *Immunogenetics 40*:331–338 (1994).

Alving, et al., "Association Between Histamine–Containing Mast Cells and Sensory Nerves in the Skin and Airways of Control and Capsaicin–Treated Pigs," *Cell Tissue Res. 264*:529–538 (1991).

Beauvais, et al., "Dipeptidyl–Peptidase IV Secreted by *Aspergillus fumigatus*, a Fungus Pathogenic to Human," *Infection and Immunity 65*:3042–3047 (1997).

Darmoul, et al., "Dipeptidyl Peptidase IV (CD 26) Gene Expression in Enterocyte–Like Colon Cancer Cell Lines HT–29 and Caco–2," *J. Bio. Chem. 267*:4824–4833 (1992).

Duke–Cohan, et al., "Attractin (DPPT–L), a Member of the CUB Family of Cell Adhesion and Guidance Proteins, Is Secreted by Activated Human T Lymphocyte and Modules Immune Cell Interactions," *Proc. Natl. Acad. Sci. USA 95*:11336–11341 (1998).

Heymann, et al., "Liver Dipeptidyl Aminopeptidase IV Hydrolyzes Substances P," *FEBS Letters 91*:360–364 (1978).

Hua, et al., "Pharmacology of Calcitonin Gene Related Peptide Release from Sensory Terminal in the Rat Trachea," *Can. J. Physiol. Pharmacol. 73*:999–1006 (1995).

Lundblad, "Protective Reflexes and Vascular Effects in the Nasal Mucosa Elicited by Activation of Capsaicin–Sensitive Substance P–Immunoactive Trigeminal Neurons," *Acta Physiol. Scand. 529*:1–42 (1984).

Mentlein, et al., "Proteolytic Processing of Neuropeptide Y and Peptide YY by Dipeptidyl Peptidase IV," *Reg. Peptides 49*:133–144 (1993).

Misumi, et al., "Molecular Cloning and Sequence Analysis of Human Dipeptidyl Peptidase IV, a Serine Proteinase on the Cell Surface," *Biochimica et Biophysica Acta. 1131*:333–336 (1992).

Nagase, et al., "Prediction of the Coding Sequences of Unidentified Human Genes. IX. The Complete Sequences of 100 New cDNA Clones from Brain Which Can Code for Large Proteins in vitro," *DNA Res. 5*:31–39 (1998).

Nakata, et al., "Active Uptake of Substance P Carboxy–Terminal Heptapeptide (5–11) into Rat Brain and Rabbit Spinal Cord Slices," *J. Neurochem. 37*:1529–1534 (1981).

Nieber, et al., "Substances P and β–Endorphin–Like Immunoreactivity in Lavage Fluids of Subjects With and Without Allergic Asthma," *J. Allergy Clin. Immunol. 90*:646–652 (1992).

Sakurada, et al., "Major Metabolites of Substances P Degraded by Spinal Synaptic Membranes Antagonized the Behavorial Response to Substance P in Rats," *J. Pharm. Sci. 88*:1127–1132 (1999).

Sannes, "Subcellular Localization of Dipeptidyl Peptidases II and IV in Rat and Rabbit Alveolar Macrophages," *J. Histochem. Cytochem. 31*:684–690 (1983).

Saria, et al., "Release of Multiple Tachykinins from Capsaicin–Sensitive Sensory Nerves in the Lung by Bradykinin, Histamine, Dimethylphenyl Piperazinium, and Vagal Nerve Stimulation," *Am. Rev. Respir. Dis. 137*:1330–1335 (1988).

Stead, et al., "Neuropeptide Regulation of Mucosal Immunity," *Imm. Rev. 100*:333–359 (1987).

Stjärne, et al., "Release of Calcitonin Gene–Related Peptide in the Pig Nasal Mucosa by Antidromic Nerve Stimulation and Capsaicin," *Reg. Peptides 33*:251–262 (1991).

Svensson, et al., "Albumin, Brandykinins, and Eosinophil Cationic Protein on the Nasal Mucosal Surface in Patients with Hay Fever During Natural Allergin Exposures," *J. Allergy Clin. Immunol. 85*:828–833 (1990).

Underwood, et al., "Sequence, Purification, and Cloning of an Intracellular Serine Protease, Quiescent Cell Proline Dipeptidase," *J. Biol. Chem. 274*:34053–34058 (1999).

Van Der Velden, et al., "Expression of Aminopeptidas N and Dipeptidyl Peptidase IV in the Healthy and Asthmatic Bronchus," *Clin. Experi. Allergy 28*:110–120 (1998).

Vasko, et al., "Prosataglandin E2 Enhances Bradykinin–Stimulated Release of Neuropeptides from Rat Sensory Neurons in Culture," *J. Neurosci. 14*:4987–4997 (1994).

*Primary Examiner*—David M. Naff
*Assistant Examiner*—Mike Meller
(74) *Attorney, Agent, or Firm*—Michael A. Sanzo; Pillsbury Winthrop LLP

(57) ABSTRACT

The present invention is directed to methods of treating mucosal inflammation associated with rhinitis or sinusitis by administering peptidases that recognize and cleave polypeptides at Xaa-Pro sequences. In addition, the invention encompasses therapeutic packages in which pharmaceutical compositions containing the peptidases are preloaded in a device suitable for intranasally delivering drug.

8 Claims, No Drawings

METHOD OF TREATING RHINITIS OR SINUSITIS BY INTRANASALLY ADMINISTERING A PEPTIDASE

FIELD OF THE INVENTION

The present invention is directed to methods of treating inflammation associated with rhinitis or sinusitis by intranasally delivering peptidases to a patient. The invention also encompasses therapeutic packages in which a peptidase is preloaded in a device designed for intranasally delivering drug.

BACKGROUND OF THE INVENTION

Rhinitis, an inflammation of the nasal mucosal membrane, is characterized by sneezing, rhinorrhea, nasal congestion, and increased nasal secretion. It is often accompanied by sinusitis, an inflammation of the sinuses. When these conditions persist for a period of more than three weeks, they are termed "chronic." More than 37 million Americans, particularly those with allergies or asthma, suffer from these conditions, making them the most common chronic medical problems in the United States.

Chronic "rhinosinusitis" or sinusitis is difficult to treat successfully. In general, treatment consists of a combination of antibiotics and decongestants or antihistamines. In addition, steroid nasal sprays are commonly used to reduce inflammation. For patients with severe chronic sinusitis, oral steroids, such as prednisone, may also be prescribed. However, the long-term safety of steroid administration, especially in children, is not fully understood and oral steroids often have significant side effects. When drug therapy fails, surgery is usually the only alternative.

The mucosal tissue lining the nasal and sinus passages is densely packed with sensory neurons (Alving, et al., *Cell Tissue Res.* 264:529–538 (1991); Saria, et al., *Am. Rev. Respir. Dis.* 147:1330–1335 (1988)). When activated, these neurons release a variety of bioactive peptides that contribute to inflammation by causing vasodilation, stimulating mucosal gland secretion, and promoting infiltration by inflammatory mast cells, lymphocytes and eosinophils (Stead, et al, *Immunol. Rev.* 10:333–359 (1987); Mygind, et al., *Eur. J Respir. Dis.* 64(S128):1–379 (1983)). Included among the released bioactive peptides are substance P, calcitonin-gene related peptide, neuropeptide Y and vasoactive intestinal peptide (Lundblad, et al., *Acta. Physiol. Scand.* 529:1–42 (1984)). Means for controlling the activity of these peptides should provide an effective treatment for the inflammation associated with both rhinitis and sinusitis.

SUMMARY OF THE INVENTION

The present invention stems from the discovery that dipeptidyl peptidase IV, an exopeptidase that cleaves Xaa-Pro dipeptides from the N-terminus of polypeptides, is present in human nasal mucosa at levels that are inversely related to inflammation. Thus, low levels of dipeptidyl peptidase IV are associated with a high density of inflammatory cells, and high levels of dipeptidyl peptidase IV are associated with a low density of inflammatory cells. This is important because dipeptidyl peptidase IV degrades peptides that contribute to the pathophysiology of rhinitis, sinusitis and asthma (Mentlein, et al., *Regul. Peptides* 49:133–144 (1993); Heymann, et al, *FEBS Lett.* 91:360–364 (1978); Beauvais, et al., *Fum. Infect. Immun.* 65:3042–3047 (1997)). Among the inflammation-related peptides cleaved are NPY, SP, and desArg1 bradykinin. Based upon these observation and further experiments, the concept has been developed that the intranasal administration of dipeptidyl peptidase IV can reduce inflammation in the mucosal tissue that lines both the nasal cavity and sinuses. Other proteases that possess the same proteolytic activity should also produce a positive therapeutic effect. These proteases include quiescent cell proline dipeptidase (Underwood, et al., *J. Biol. Chem.* 274:34053–34058 (1999)), dipeptidyl peptidase 8 (Abbott, et al., *Eur. J Biochem.* 267:6140–6150 (2000)), and attractin (Duke-Cohan, et al., *Proc. Nat'l. Acad. Sci. U.S.A.* 95:11336–11341 (1998)).

In its first aspect, the invention is directed to a method of treating a patient for inflammation of the nasal or sinus mucosa. The method involves intranasally administering a therapeutically effective amount of a peptidase (preferably an exopeptidase) that cleaves at Xaa-Pro residues, where Xaa represents any of the 20 amino acids commonly found in animals. A "therapeutically effective" dose is defined as an amount sufficient to produce a significant reduction in inflammation as evidence by either a reduced number of inflammatory cells in mucosal tissue or by a significant improvement in one or more symptoms associated with the inflammation. For example, in the case of rhinitis or sinusitis, a therapeutically effective dose would be a sufficient amount to produce a significant reduction in sneezing, coughing, sinus-related headaches, nasal obstruction, mucosal secretion, or other discomfort associated with these conditions. Inflammatory cells include mast cells, lymphocytes and eosinophils. In general, it is expected that a therapeutically effective dose for any of the proteases used will be between 1 microgram and 1 milligram and, typically, between 5 micrograms and 500 micrograms.

The preferred peptidase for use in the method is dipeptidyl peptidase IV. Other peptidases that can be used include quiescent cell proline dipeptidase; dipeptidyl peptidase 8, and attractin. In each case, it is the human form of the peptidase that is preferred. However, peptidases from other species (e.g., that secreted by *Aspergilus Fumigatus,* see Examples section) may also be used provided that they have the ability to cleave at the Xaa-Pro sequence. Although the method will work for rhinitis and sinusitis caused by any disease or condition, it is expected that the most common causes will be allergies or asthma.

In another aspect, the invention is directed to a therapeutic package in which a device for intranasally delivering drug to a patient is preloaded with a solution or powder containing one or more of the peptidases described above. The invention is compatible with any intranasal delivery device (including encapsulated dosage forms) and with any of the numerous compositions that have been described for delivering drugs by means of the nasal cavity. When liquid compositions are used in the device, it is expected that peptidase will be present at a concentration of between 1 µg/ml and 10 mg/ml, and more typically, at a concentration of between 10 µg/ml. and 1 mg/ml.

The invention also encompasses the concept that SP is particularly important in causing inflammation in lung and nasal mucosa. Any method that reduces the local activity of this peptide should be useful in the treatment of rhinitis or sinusitis. A reduction in activity may be accomplished either using a peptidase that degrades SP (e.g., one of the peptidases described above) or by administering an agent that inhibits the binding of SP to the NK1 receptor (see Examples section).

DETAILED DESCRIPTION OF THE INVENTION

A. Preparation of Peptidases

The present invention is directed to treatment methods which utilize peptidases that have the common characteristic of cleaving at Xaa-Pro sites. These may be purchased commercially or obtained using any of the procedures described in the relevant literature. For example, the gene corresponding to the peptidase can be isolated and used for recombinant protein production. Especially preferred peptidases, along with references relevant to their isolation and recombinant production, are: human dipeptidyl peptidase IV, shown herein as SEQ ID NO: 1 (Misumi, et al, *Biochim. Biophys. Acta* 15:1131 (1992); Darmoul, et al., *J. Biol. Chem.* 267:4824–4833 (1992); Abbott, et al., *Immunogenetics* 40:331–338 (1994)); human quiescent cell proline dipeptidase, shown herein as SEQ ID NO: 2 (Underwood, et al, *J. Biol. Chem.* 274:34053–34058 (1999)); human attractin, shown herein as SEQ ID NO: 3 (Duke-Cohan, et al., *Proc. Nat'l. Acad. Sci. USA* 95:11336–11341 (1998); Nagase, et al, *DNA Res.* 5:31–39 (1998)); and human dipeptidyl peptidase 8, shown herein as SEQ ID NO: 4 (Abbott, et al., *Eur. J. Biochem.* 267:6140–6150 (2000)). In addition to being made recombinantly, these proteins can be synthesized using methods that are well-known in the art.

B. Making of Pharmaceutical Compositions

Compositions for intranasally delivering peptidases can be made in accordance with methods that are standard in the art (see, e.g., *Remington's Pharmaceutical Sciences*, 16$^{th}$ ed. A. Oslo Editor, Easton, Pa. (1980)). Enzymes will typically be prepared in admixture with conventional excipients. Suitable carriers may include, but are not limited to: water; salt solutions; alcohols; vegetable oils; polyethylene glycols; gellatin; carbohydrates such as lactose, amylose or starch; talc; hydroxymethylcellulose etc. The pharmaceutical preparations can be sterilized and, if desired, mixed with auxiliary agents such as preservatives or stabilizers. The invention is compatible with any of the numerous compositions that have been disclosed in the art for nasal delivery including those in: U.S. Pat. Nos. 6,054,462; 4,946,870; 5,897,858; and 4,476,116. The concentration of peptidase present can vary over a wide range. Typically, in liquid formulations, peptide should be present in an amount of between 1 µg/ml and 10 mg/ml and, more commonly, at a concentration of between 10 µg/ml and 1 mg/ml.

Treatment Methods

The present invention is directed to methods for treating inflammation present in the mucosal lining of the nasal or sinus passages. It depends upon the direct administration of sufficient peptidase to proteolytically cleave peptides known to contribute to inflammation. The total dosage of peptidase to be administered to a patient should be at least the amount required to achieve this objective as reflected by a reduction or elimination of symptoms associated with inflammation. For example, a patient being treated for rhinosinusitis should receive sufficient compound to reduce or eliminate the frequency or intensity of sinus headache, reduce coughing, congestion, sneezing, respiratory obstruction or other discomforts associated with the condition.

In general, a patient may begin by self-administering a relatively small dose of compound and then repeat administration as necessary. For example, a patient may begin by administering 0.1 mg per day and then increase the dosage upward using changes in inflammation-related symptoms as a guide. Typically, it is expected that patients will receive a daily dose of between 1 µg and 1 mg per day, and, more typically, between 5 µg and 500 µg. Daily dosages may be provided in either a single or multiple regimen with the latter being generally preferred. These are simply guidelines, since the actual dose will be determined by the patient and their physician based upon a variety of clinical factors.

Therapeutic Packages

In addition to the pharmaceutical compositions described above, the invention includes therapeutic packages for the intranasal delivery of the compositions. A therapeutic package is comprised of a device designed for the intranasal inhalation of medication which has been preloaded with a pharmaceutical composition containing one or more of the peptidases described above. In general, spray devices are preferred, such as those disclosed in U.S. Pat. No. 6,145,703; WO 95/00195; U.S. Pat. No. 5,307,953; EP 0388651; U.S. Pat. Nos. 4,017,007; 5,301,846; 3,176,883; or 4,286,735. Devices for administering powders or nasal drops may also be used. When the pharmaceutical composition is in the form of a solution, it is expected that peptidase should generally be present at a concentration of between 1 µg/ml and 10 mg/ml, and, more typically, at a concentration of between 10 µg/ml and 1 mg/ml.

EXAMPLES

I. Materials and Methods

Recombinant Dipeptidyl Peptidase IV (DPPIV)

A soluble form of DPPIV secreted from *Aspergilus Fumigatus* has been previously characterized and was used in the present experiments (Beauvais et al., *Infection Immun.* 65 3042–3047 (1997)). The enzyme has an apparent molecular weight of 95 kDa. It was expressed in the yeast *Pichia Pastoris* and purified to more than 99% purity as assessed by electrophoresis and gel-filtration to reach a specific activity of 40 units/mg of protein. SP (1.8 µg) co-incubated with 0.016 µg of DPPIV for ten minutes at 37° C. is degraded to SP5–11 as identified by mass-spectrometry. If an excess of SP is added (3.5 µg) a partial of digestion of the peptide is observed.

Patients

Forty-five patients, 23 males and 22 females, suffering from nasal obstruction, rhinorrhea and headaches for more than eighteen months were included in the study. Pre-operative rhinoscopy revealed septal deviation associated with concha bullosa of the middle turbinate. All patients underwent septoplasty and partial middle turbinectomy under endoscopic control with general anesthesia. The age range was 14 to 64 years with the average patient being 39 years of age. Patients with allergy, nasal polyps or tumors were excluded.

Tissue Processing

Samples of middle turbinate mucosa from patients undergoing partial turbinectomy were fixed immediately in ice cold acetone with 2 mM phenyl methyl sulphonyl fluoride and 20 mM iodoacetamide and incubated overnight at −20° C. Biopsies were embedded in glycol methacrylate resin and allowed to polymerize overnight at 4° C.

Antibodies

The following monoclonal antibodies were used: CD26 (clone BA5, DAKO) directed against DPPIV protease, diluted 1:20; CD1A (Biogenex) for dendritic cells, diluted 1:20; CD31 (DAKO) recognizing the adhesion molecule PECAM on endothelial cells, diluted 1:20; and the polyclonal antibody CD3 (DAKO) directed against T cells and used at a dilution of 1:20.

Immunohistochemical Staining

Serial sections, 2 mm thick, were cut using a Reichert-ung microtome equipped with a glass knife. Immunohistochemical staining was performed using the streptavidin biotin-peroxidase method with aminoethyl-carbazole (AEC) as substrate.

Quantification of Inflammation in Nasal Biopsies and Intensity of Symptoms

Mucosal samples of the middle turbinate from both sides (N=90) were fixed in formaldehyde and dehydrated, embedded in paraffin, and colored by haematoxylin-eosin. They were then examined under a Zeiss microscope at 40× magnification. Histological analysis included defining the integrity of the pseudo-stratified columnar epithelium, noting the presence or absence of edema and quantifying the number of inflammatory cells within the submucosa. This was accomplished using a scale graded from 0 to +++, where 0 meant no inflammatory cells and +++ represented abundant inflammatory cells. Using the Rank Spearman correlation test, the correlation between DPPIV and the degree of inflammation of the nasal mucosa was examined. The intensity of nasal obstruction, rhinorrhea and headache was recorded by means of a visual analog scale graded from 0 to 5, where 0 corresponds to the absence of symptoms and 5 corresponds to severely intense symptoms. Nasal airway resistance was recorded by means of anterior rhinomanometry (rhinotest).

The Determination of DPPIV Activity in Human Mucosa Biopsies

DPPIV activity was determined according to Scharpe, et al. (*Clin. Chim. Acta* 195: 125–132 (1990)) with the following modifications: nasal biopsies were sonicated in the presence of 0.5 ml of 100 mM Tris-HCl, pH 8, for 2 minutes on ice using a Branson sonifier (output 4) and centrifuged for 10 minutes at 15,000 rpm in a microfuge at 4° C. The supernatant was recovered and the pellet was treated with 0.5 ml of 100 mM Tris-HCl, pH8, containing 2% Triton X100. The suspension was vortexed for one minute and centrifuged for 10 minutes at 15,000 rpm in a microfuge at 4° C. The supernatant was recovered, pooled with the one obtained previously, and stored at −20° C. DPPIV activity was determined on 1, 2.5 and 5 μl of supernatant fluorometrically using Gly-Pro-AMC (Novabiochem) at 5 mM final concentration for 60 minutes at 37° C. under agitation in an Eppendorf thermomixer in 25 μl of 100 mM Tris-HCl, pH 8. The reaction was stopped by the addition of 2.5 μl of pure acetic acid. The incubation mixture was recovered in 3 ml of water. A blank value was obtained by incubating the substrate in the absence of enzyme and a standard curve was determined using AMC fluorescence measurement on a fluorometer. The DPPIV activities were standardized based on wet tissue weight and specific activities expressed as pmoles of substrate converted per mg of tissue per minute.

Experiments in the Pig In Vivo

Experiments were performed on pigs of both sexes (body weight 18–25 kg). All animals were premedicated with atropine (0.05 mg/kg) and ketamine (20 mg/kg i.m.). They were anesthesized with thiopentone (5 mg/kg i.v.). After tracheostomy, animals were intubated and artificially ventilated by a volume regulated ventilator. During surgery, animals were given a continuous i.v. infusion of Ringer's solution, pancuronium bromide (0.25 mg/kg) and heparin. Each experiment lasted approximately 8 hours. Catheters were placed in the femoral artery for systemic blood pressure and heart rate monitoring and in the femoral vein for thiopentone, heparin and fluid administration (300 ml/hr). The contralateral femoral vein was canulated for blood sampling. Surgical preparation of the internal maxillary artery was done in accordance with Lacroix (*Acta Physiol. Scand.* 136:1–63 (1989)). Selective recording of the nasal arterial blood flow was performed with a Transonic flow probe (probe 2.4RB143) of 2.4 mm diameter placed around the sphenopalatine artery. The flow probe was connected to a T202S ultrasonic blood flowmeter. All the arterial branches situated downstream of the flow probe were ligated and cut except for the superficial temporal artery which was cannulated with a PE 90 catheter for infusions or injections.

Variations in the area under the curve (AUC) of the sphenopalatine artery vascular resistance (Vr), derived from both mean arterial blood pressure and systemic blood flow curves, were analyzed over time. Durations of the responses of the vascular resistance were compared and all results were expressed in percent of baseline. Vascular parameters were recorded simultaneously using a 6 pen trace recorder.

All animals were intranasally administered DPIV (50 μg, 26.5 pmoles/kg), subjected to sympathetic nerve stimulation (SNS, 15 V, 5 ms, 10 Hz for 2 minutes) and then infused with histamine (0.1–25 μg), capsacin (0.01–25 μg), bradykinin (0.001–10 μg), SP or its C-terminal fragment SP 5–11, DPPIV, or NK1 antagonist L733060 in the superficial temporal artery under controlled conditions. In each case, the vascular response of the animal was measured. This entire procedure was then repeated after local i.a. pretreatment with the alpha-adrenergic receptor antagonist phenoxybenzanime (1 mg/kg).

Vascular Responses to DPPIV in Domestic Pigs In Vivo

The basal blood flow in the internal maxillary artery of the pig under control conditions was $4.92+/-0.7$ ml min$^{-1}$ kg$^{-1}$. After section of the sympathetic nerves on the left side, the homolateral nasal arterial flow was $6.1+/-0.26$ ml min$^{-1}$ kg$^{-1}$ (representing a 19.34% +/−4.3% increase). The mean arterial blood pressure (MAP) was not modified by the section of the sympathetic nerves. Electrical stimulation of the sympathetic nerve induced a frequency-depended increase of the SVR whereas the MAP was not significantly modified. Sympathetic nerve stimulation at 10 Hz for 5 minutes reduced the blood flow in the maxillary artery from $4.92+/-0.7$ ml min$^{-1}$ kg$^{-1}$ to $1.40+/-0.47$ ml min$^{-1}$ kg$^{-1}$, representing an increase in SVR of 71.5% and lasting more than 6 minutes. The i.a. infusion of phenoxybenzamine induced a MAP reduction of 10+/−2%. The basal blood flow in the sphenopalatine artery, the heart rate and the MAP were not significantly affected by the administration of exogenous dipeptidyl peptidase IV.

Statistical Analysis

All values were expressed in terms of mean +/− SEM. Statistical analysis was done by analysis of variance, ANOVA. A value of p<0.05 was taken as statistically significant.

II. Results

DPPIV is Expressed in Endothelial Cells and Submucosal Seromucus Glands from Patients Using immunohistochemistry, DPPIV-like immunoreactivity (–LI) was detected in submucosal seromucus glands and leukocytes. In submucosal seromucus glands, DPPIV-LI appeared to be located in the apical position. Endothelial cells in blood vessels expressed weak DPPIV-LI. Some epithelial cells located in the human nasal mucosa were also DPPIV positive. However, these cells did not show any positive immunoreactivity for CD1A and Protein 100, suggesting they were not Langerhans cells.

Correlation Between DPPIV and Inflammation in the Human Nasal Mucosa

Nasal mucosa biopsies were sampled from both nostrils in 45 patients suffering from rhinosinusitis to determine if DPPIV activity was affected by the mucosal inflammation. DPPIV activity was found to vary from undetectable to 707 pmol/min/mg. Histological analysis revealed marked differences in the density of inflammatory cells within the submucosa of the nasal biopsies studied. A low activity of DPPIV was associated with a high density of inflammatory cells in the nasal mucosa of patients with chronic rhinosinusitis. When the density of inflammatory cells observed was plotted against DPPIV activity, the regressive correlation was found to be statistically significant (p<0.001). Nasal mucosa samples obtained from smokers exhibited a significantly lower DPPIV activity than samples obtained from non-smokers having the same low density of inflammatory cells (p<0.01).

When the density of inflammatory cells in each biopsy was plotted against the subjective evaluation of nasal obstruction, the data fitted a statistically significant correlation (p<0.01), suggesting that nasal inflammation increased in parallel with subjective nasal obstruction severity. In addition, nasal mucosa biopsies were obtained from 10 patients with significant improvement of their symptoms (p<0.001), 6 months after endonasal surgery. The DPPIV activity was significantly increased in all of the samples studied when compared to the preoperative state (p<0.001) indicating that DPPIV activity can be restored when chronic rhinosinusitis is cured. Since there was a clear negative correlation between DPPIV activity and nasal mucosal inflammation, the hemodynamic effect of SP in the presence of recombinant DPPIV was studied in pig nasal mucosa.

DPPIV Modulates Inflammatory Response Mediated by Histamine in Pigs

Histamine is responsible for the early-phase allergic reaction and exerts both direct and indirect effects on sensory nerves, glands and blood vessels of the nasal mucosa (Alving, *Acta. Physiol. Scand.* 597:1–64 (1991)). There is direct evidence that histamine can release peptides from capsaicin sensitive sensory nerves in the lung by activation of $H_1$-receptors (Alving, et al., *Acta. Physiol. Scand.* 138:49–60 (1990)). In addition, endogenous or exogenous histamine stimulates sensory fibers, possibly by acting on specific receptors to increase the release of CGRP and SP (Tani, et al., *Neurosci. Lett.* 115:171–176 (1990).

Histamine i.a. local injection following sympathetic nerve stimulation (SNS) at 10 Hz for 5 minutes showed a significant reduction in duration at $5.4 \times 10^{-09}$ moles (33%) and at $1.4 \times 10^{-07}$ moles (32%) when compared to control conditions. After i.a. administration of 50 µg of DPPIV and SNS, histamine challenge showed no significant variation in the area under the curve (AUC) or vascular resistance (Vr) when compared to control. However, the duration of histamine effect was reduced by 33.7% at a dose of $5.4 \times 10^{-08}$ moles (p<0.05) and by 50.7% at a dose of $1.4 \times 10^{-07}$ moles (p<0.01). After phenoxybenzamine (PBZ) pretreatment, DPPIV and SNS, histamine vasodilatory effects were markedly reduced. When compared to control, the AUC showed a reduction of 81.9% at a dose of $5.4 \times 10^{-08}$ moles (p<0.001) and a reduction of 81.8% at a dose of $1.4 \times 10^{-07}$ moles (p<0.001). Vr showed a reduction of 67.9% at $5.4 \times 10^{-08}$ moles (p<0.01) and a reduction of 61.1% at $1.4 \times 10^{-07}$ moles (p<0.05). Duration of effect was also reduced at doses of $5.4 \times 10^{-09}$ moles (42.6%, p<0.01); $5.4 \times 10^{-08}$ moles (55.6%, p<0.001); and $1.4 \times 10^{-07}$ moles (62.5%, p<0.001).

DPPIV Modulates the Vasodilation Evoked by Capsaicin in Pigs

Capsaicin (8-methyl-N-vanillyl-6-nonenamide), by activating unmylinated sensory C-fibers, acts in many respects like histamine. Capsaicin has been shown to release tachykinins (Hua, et al., *Neurosci.* 19:313–319 (1986)) as well as CGRP (Stjarne, et al, *Regul. Pept.* 33:251–262 (1991)) both in vitro and in vivo. Capsaicin injection following SNS showed a dose-dependent decrease of Vr similar that to observed under control conditions. The vasodilatory effect of capsaicin after SNS and PBZ pretreatment showed no significant variation at any doses. However, the duration of vasodilation evoked at $8.2 \times 10^{-08}$ moles was significantly reduced (39.9%, p<0.01) and AUC was reduced by 26.6% at $8.2 \times 10^{-08}$ moles (p<0.05). Capsaicin effects were also modified after DPPIV and SNS. The AUC observed at a dose of $8.2 \times 10^{-08}$ moles showed a reduction by 56.6% (p<0.01). The Vr response was reduced by 34.8% (p<0.05) and the duration of effect at doses of $3.3 \times 10^{-09}$ moles and $8.2 \times 10^{-08}$ mol was reduced by 55.4% (p<0.05) and 50.5% (p<0.001) respectively. After PBZ, DPPIV and SNS, there was marked reduction in Vr, duration of effect, and AUC. Vr at $8.2 \times 10^{-08}$ moles was reduced by 39.9% (p<0.01). At $3.3 \times 10^{-09}$ moles and $8.2 \times 10^{-08}$ moles, the duration of the vascular response was reduced by 64.3% (p<0.05) and 56.8% (p<0.001). At $8.2 \times 10^{-08}$ moles, AUC was reduced by 66.7% (p<0.01).

DPPIV Modulates the Vasodilatory Response Mediated by Bradykinin in Pigs

Bradykinin (BK) is a polypeptide involved in nociception and humoral regulation of vascular tonicity and permeability. BK produces marked vasodilation, increases capillary permeability and is involved in most inflammatory reactions, including rhinitis (Svensson, et al., *J. Allergy Clin. Immunol.* 85:828–833 (1990)). Like histamine and capsaicin, BK stimulates nociceptive sensory nerves to produce CGRP and SP (Hua, et al., *Can. J. Physiol, Pharmacol.* 73:999–1006 (1995); Vasco, et al., *J. Neurosci.* 14:4987–4997 (1994)).

BK injection following SNS showed a dose-dependent decrease of Vr similar to that observed under control conditions. After DPPIV and SNS, BK showed only variation in the duration of effect at doses of $9.4 \times 10^{-11}$ moles (34%, p<0.01) and $9.4 \times 10^{-09}$ moles (38.3%, p<0.001). After PBV, DPPIV and SNS, vascular parameters were reduced to a smaller extent than that seen with histamine and capsaicin. For example, AUC after i.a. administration of BK was reduced by 29.3% at $9.4 \times 10^{-09}$ moles (p<0.01) and by 40% at $9.4 \times 10^{-11}$ mol (p<0.01). At $9.4 \times 10^{-10}$ moles duration of effect was reduced by 32.2% (p<0.05) and at $9.4 \times 10^{-09}$ moles, duration was reduced by 39.4% (p<0.001).

DDPIV Modulates the Vasodilatory Response Mediated by SP in Pigs

Repeated injection of high doses of SP caused a reproducible decrease in sphenopalatine vascular resistance, indicating that the desensitization of neurokinin (NK) receptors did not occur. Therefore, the same animal was used to perform dose-response curves with SP both before and after pretreatment with DPPIV. A dose-response curve for duration of vasodilation and area under the curve was constructed using doses of SP in the range of 1 pg to 0.1 µg. A reproducible dose-response curve was obtained over a 45 minute period using 6 doses of SP. Vasodilation ranged from 15.1% +/−3.3% to 37.3% +/−3.3% after local intraarterial administration of 1 pg and 100 ng of SP respectively. To determine whether vasodilation evoked by SP was affected by pretreatment with DPPIV, two doses of SP (100 pg and 1 ng) were administered and a reduction in SVR of 13.1% and 14.9% was observed. The same animals received 50 µg (530 pmoles) of DPPIV and similar doses of SP were injected. Recombinant DPPIV had no vascular effect per se. Subsequent administration of the SP resulted in a dramatic diminution of SP-evoked vasodilatory response (by 66 and 71% respectively) when compared to controls. Since DPPIV cleaves SP into SP 5–11, experiments were conducted to determine whether SP 5–11 is also capable of decreasing SVR. Similar to what was observed with respect to SP, a dose response curve was obtained with 10 pg to 1 μg of SP 5–11 (5 to 35% decrease in SVR respectively). However, the vasodilatory effect of SP 5–11 was considerably lower when compared to SP. Based on molarity, SP is 200 fold more potent than SP 5–11 as a vasodilator. Therefore, DPPIV administration to pigs might result in an almost immediate conversion of SP 5–11.

To further characterize the nature of neurokinin receptor subtype involved in the reduction of SVR, pigs were pretreated with a NK1 antagonist, L-733060, at 114 nmoles/kg to evaluate the blockade of SP-induced decreased in SVR. It was found that the antagonist has a vasoconstrictive effect. A clear inhibition of the SP effect was observed at all doses of SP used except 100 ng. Thus, the SP effect on SVR is likely to mediated by the NK1 receptor.

III. Discussion

The localization of the enzyme DPPIV in the apical position of nasal exocrine cells in seromucus glands suggests a role of this enzyme in the protective function of nasal mucus. The presence of DPPIV in vascular endothelial cells and T-cells is in line with earlier histochemical studies of DPPIV in mammmalian tissue (Sannes, *J. Histochem. Cytochem.* 31:684–690 (1983)) as well as with more recent reports on the distribution of human DPPIV (Van. Der. Elden, et al, *Clin. Exp. Allergy* 28:110–120 (1998)). DPPIV immunoreactivity was also observed in some intraepithelium cells of nasal mucosa. These cells were probably not Langerhans cells since they did not express CD1A or Protein 100 immunoreactivity on their surface.

Correlation between DPPIV activity and inflammation of nasal mucosa showed a marked decrease of enzyme activity in the presence of severe inflammation. In agreement with Van der Velden, et a. (Id.), who showed that DPPIV activity is reduced in the serum of healthy smokers compared to non-smokers, DPPIV activity was reduced ill nasal samples with severe inflammation. In contrast, high DPPIV enzymatic activity was correlated with a small number of inflammatory cells in the nasal mucosa. The fact that enzyme activity increased after treatment of chronic rhinosinusitis is also consistent with the involvement of the enzyme in this pathology. Pretreatment with 50 μg of DPPIV significantly decreased duration of vasodilation and spenopalatine artery vascular resistance when DPPIV was used alone or with the adrenoreceptor blocker phenoxybenzamine.

DPPIV significantly decreased both peak and duration of the vasodilation evoked by SP. It was found that the SP 5–11 was at least 100 fold less potent than SP at causing vasodilation. These results suggest that a lost of DPPIV expression occurs during chronic rhinosinusitis and that the resulting reduction of SP degradation contributes to the maintenance of nasal mucosa inflammation. In this regard, Nieber, et al have shown that allergic patients have higher baseline levels of SP-ir in nasal lavage fluids than non-allergic controls and that intranasal allergen increases SP levels in nasal lavage fluids only in subjects with grass pollen allergy (*J. Allergy Clin. Immunol.* 4 p1:646–652 (1992)). The antibody used for the SP assay in the Nieber study required both an intact N- and C-terminus peptide sequence. The data is in line with that presented herein and could be explained by the fact that allergic patients expressing less DDPIV than normal volunteers produce intact SP which could be measured by their antibody. In contrast, normal volunteers cleave their SP into SP 5–11 fragments which are no longer detected in the SP assay. SP effects on the vascular bed of the nasal mucosa are maintained only when allergenic stimulation persists in subjects with nasal allergies (i.e., subjects without DPPIV).

In parallel to SP cleavage by DPPIV into SP 5–11, a N-terminal fragment, SP 1–4, is generated and has been reported to exert an antagonist affect on SP action (Sakurada, et al., *J. Pharm. Sci.* 88: 1127–1132 (1999)). Thus, DPPWV might modulate SP action, not only by producing a less active NK1 agonist, but also by interfering with SP effects. Since SP 5–11 (but not SP) is subject to cellular uptake, DPPWV may also act to terminate the action of SP via conversion to a form which is removed by cellular processes (Nakata, et al., *J. Neurochem.* 37:1529–1534 (198 1)). Once SP is cleaved by DPPWV into SP 5–11, this fragment is further processed with a high efficiency by aminopeptidase M into inactive fragments. Thus, DPPIV first converts SP to a much less active form, SP 5–11, which is then completely inactivated by the action of aminopeptidase M. Finally, DPPIV could potentially act upon other peptides which are known to be involved in promoting inflammation and which have structures that lend themselves to degradation by this enzyme.

All references cited are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of treating a patient for mucosal inflammation associated with rhinitis, sinusitis or both, comprising: intranasally administering to said patient a therapeutically effective amount of a peptidase that cleaves at Xaa-Pro sequences.

2. The method of claim 1, wherein said peptidase is an exopeptidase selected from the group consisting of: dipeptidyl peptidase IV, quiescent cell proline dipeptidase, dipeptidyl peptidase 8, and attractin.

3. The method of claim 2, wherein said exopeptidase is dipeptidyl peptidase IV.

4. The method of claim 2, wherein said exopeptidase is dipeptidyl peptidase 8.

5. The method of claim 2, wherein said exopeptidase is quiescent cell proline dipeptidase.

6. The method of claim 2, wherein said exopeptidase is attractin.

7. The method of claim 2, wherein said exopeptidase is administered at a dose of between 1 $\mu$g and 1 mg.

8. The method of any one of claims 1–7, wherein said rhinitis, sinusitis or both, is the result of allergies or asthma.

* * * * *

SEQUENCE LISTING

```
<160> NUMBER OF SEQ ID NOS: 4

<210> SEQ ID NO 1
<211> LENGTH: 766
<212> TYPE: PRT
<213> ORGANISM: Homo sapiens

<400> SEQUENCE: 1

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60
```

-continued

```
Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480
```

-continued

```
Thr Leu His Ser Ser Val Asn Asp Lys Gly Leu Arg Val Leu Glu Asp
            485                 490                 495

Asn Ser Ala Leu Asp Lys Met Leu Gln Asn Val Gln Met Pro Ser Lys
        500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
        610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
        690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 2
<211> LENGTH: 492
<212> TYPE: PRT
<213> ORGANISM: Homo sapiens

<400> SEQUENCE: 2

Met Gly Ser Ala Pro Trp Ala Pro Val Leu Leu Leu Ala Leu Gly Leu
1               5                   10                  15

Arg Gly Leu Gln Ala Gly Ala Arg Arg Ala Pro Asp Pro Gly Phe Gln
            20                  25                  30

Glu Arg Phe Phe Gln Gln Arg Leu Asp His Phe Asn Phe Glu Arg Phe
        35                  40                  45

Gly Asn Lys Thr Phe Pro Gln Arg Phe Leu Val Ser Asp Arg Phe Trp
    50                  55                  60

Val Arg Gly Glu Gly Pro Thr Phe Phe Tyr Thr Gly Asn Glu Gly Asp
65                  70                  75                  80

Val Trp Ala Phe Ala Asn Asn Ser Gly Phe Val Ala Glu Leu Ala Ala
                85                  90                  95
```

-continued

```
Glu Arg Gly Ala Leu Leu Val Phe Ala Glu His Arg Tyr Tyr Gly Lys
                100                 105                 110
Ser Leu Pro Phe Gly Ala Gln Ser Thr Gln Arg Gly His Thr Glu Leu
            115                 120                 125
Leu Thr Val Glu Gln Ala Leu Ala Asp Phe Ala Glu Leu Leu Arg Ala
        130                 135                 140
Leu Arg Arg Asp Leu Gly Ala Gln Asp Ala Pro Ala Ile Ala Phe Gly
145                 150                 155                 160
Gly Ser Tyr Gly Gly Met Leu Ser Ala Tyr Leu Arg Met Lys Tyr Pro
                165                 170                 175
His Leu Val Ala Gly Ala Leu Ala Ala Ser Ala Pro Val Leu Ala Val
            180                 185                 190
Ala Gly Leu Gly Asp Ser Asn Gln Phe Phe Arg Asp Val Thr Ala Asp
        195                 200                 205
Phe Glu Gly Gln Ser Pro Lys Cys Thr Gln Gly Val Arg Glu Ala Phe
210                 215                 220
Arg Gln Ile Lys Asp Leu Phe Leu Gln Gly Ala Tyr Asp Thr Val Arg
225                 230                 235                 240
Trp Glu Phe Gly Thr Cys Gln Pro Leu Ser Asp Glu Lys Asp Leu Thr
                245                 250                 255
Gln Leu Phe Met Phe Ala Arg Asn Ala Phe Thr Val Leu Ala Met Met
            260                 265                 270
Asp Tyr Pro Tyr Pro Thr Asp Phe Leu Gly Pro Leu Pro Ala Asn Pro
        275                 280                 285
Val Lys Val Gly Cys Asp Arg Leu Leu Ser Glu Ala Gln Arg Ile Thr
290                 295                 300
Gly Leu Arg Ala Leu Ala Gly Leu Val Tyr Asn Ala Ser Gly Ser Glu
305                 310                 315                 320
His Cys Tyr Asp Ile Tyr Arg Leu Tyr His Ser Cys Ala Asp Pro Thr
                325                 330                 335
Gly Cys Gly Thr Gly Pro Asp Ala Arg Ala Trp Asp Tyr Gln Ala Cys
            340                 345                 350
Thr Glu Ile Asn Leu Thr Phe Ala Ser Asn Asn Val Thr Asp Met Phe
        355                 360                 365
Pro Asp Leu Pro Phe Thr Asp Glu Leu Arg Gln Arg Tyr Cys Leu Asp
370                 375                 380
Thr Trp Gly Val Trp Pro Arg Pro Asp Trp Leu Leu Thr Ser Phe Trp
385                 390                 395                 400
Gly Gly Asp Leu Arg Ala Ala Ser Asn Ile Ile Phe Ser Asn Gly Asn
                405                 410                 415
Leu Asp Pro Trp Ala Gly Gly Ile Arg Arg Asn Leu Ser Ala Ser
            420                 425                 430
Val Ile Ala Val Thr Ile Gln Gly Ala His His Leu Asp Leu Arg
        435                 440                 445
Ala Ser His Pro Glu Asp Pro Ala Ser Val Val Glu Ala Arg Lys Leu
450                 455                 460
Glu Ala Thr Ile Ile Gly Glu Trp Val Lys Ala Ala Arg Arg Glu Gln
465                 470                 475                 480
Gln Pro Ala Leu Arg Gly Gly Pro Arg Leu Ser Leu
                485                 490
```

<210> SEQ ID NO 3
<211> LENGTH: 1198

<212> TYPE: PRT
<213> ORGANISM: Homo sapiens

<400> SEQUENCE: 3

Met Val Ala Ala Ala Ala Thr Glu Ala Arg Leu Arg Arg Thr
1               5                   10                  15

Ala Ala Thr Ala Ala Leu Ala Gly Arg Ser Gly Gly Pro His Cys Val
            20                  25                  30

Asn Gly Gly Arg Cys Asn Pro Gly Thr Gly Gln Cys Val Cys Pro Ala
            35                  40                  45

Gly Trp Val Gly Glu Gln Cys Gln His Cys Gly Gly Arg Phe Arg Leu
    50                  55                  60

Thr Gly Ser Ser Gly Phe Val Thr Asp Gly Pro Gly Asn Tyr Lys Tyr
65                  70                  75                  80

Lys Thr Lys Cys Thr Trp Leu Ile Glu Gly Gln Pro Asn Arg Ile Met
                85                  90                  95

Arg Leu Arg Phe Asn His Phe Ala Thr Glu Cys Ser Trp Asp His Leu
            100                 105                 110

Tyr Val Tyr Asp Gly Asp Ser Ile Tyr Ala Pro Leu Val Ala Ala Phe
            115                 120                 125

Ser Gly Leu Ile Val Pro Glu Arg Asp Gly Asn Glu Thr Val Pro Glu
130                 135                 140

Val Val Ala Thr Ser Gly Tyr Ala Leu Leu His Phe Phe Ser Asp Ala
145                 150                 155                 160

Ala Tyr Asn Leu Thr Gly Phe Asn Ile Thr Tyr Ser Phe Asp Met Cys
                165                 170                 175

Pro Asn Asn Cys Ser Gly Arg Gly Glu Cys Lys Ile Ser Asn Ser Ser
            180                 185                 190

Asp Thr Val Glu Cys Glu Cys Ser Glu Asn Trp Lys Gly Glu Ala Cys
            195                 200                 205

Asp Ile Pro His Cys Thr Asp Asn Cys Gly Phe Pro His Arg Gly Ile
        210                 215                 220

Cys Asn Ser Ser Asp Val Arg Gly Cys Ser Cys Phe Ser Asp Trp Gln
225                 230                 235                 240

Gly Pro Gly Cys Ser Val Pro Val Pro Ala Asn Gln Ser Phe Trp Thr
                245                 250                 255

Arg Glu Glu Tyr Ser Asn Leu Lys Leu Pro Arg Ala Ser His Lys Ala
            260                 265                 270

Val Val Asn Gly Asn Ile Met Trp Val Gly Gly Tyr Met Phe Asn
            275                 280                 285

His Ser Asp Tyr Asn Met Val Leu Ala Tyr Asp Leu Ala Ser Arg Glu
    290                 295                 300

Trp Leu Pro Leu Asn Arg Ser Val Asn Val Val Arg Tyr Gly
305                 310                 315                 320

His Ser Leu Ala Leu Tyr Lys Asp Lys Ile Tyr Met Tyr Gly Gly Lys
            325                 330                 335

Ile Asp Ser Thr Gly Asn Val Thr Asn Glu Leu Arg Val Phe His Ile
            340                 345                 350

His Asn Glu Ser Trp Val Leu Leu Thr Pro Lys Ala Lys Glu Gln Tyr
            355                 360                 365

Ala Val Val Gly His Ser Ala His Ile Val Thr Leu Lys Asn Gly Arg
    370                 375                 380

Val Val Met Leu Val Ile Phe Gly His Cys Pro Leu Tyr Gly Tyr Ile
385                 390                 395                 400

```
Ser Asn Val Gln Glu Tyr Asp Leu Asp Lys Asn Thr Trp Ser Ile Leu
            405                 410                 415

His Thr Gln Gly Ala Leu Val Gln Gly Gly Tyr Gly His Ser Ser Val
        420                 425                 430

Tyr Asp His Arg Thr Arg Ala Leu Tyr Val His Gly Gly Tyr Lys Ala
        435                 440                 445

Phe Ser Ala Asn Lys Tyr Arg Leu Ala Asp Asp Leu Tyr Arg Tyr Asp
        450                 455                 460

Val Asp Thr Gln Met Trp Thr Ile Leu Lys Asp Ser Arg Phe Phe Arg
465                 470                 475                 480

Tyr Leu His Thr Ala Val Ile Val Ser Gly Thr Met Leu Val Phe Gly
                485                 490                 495

Gly Asn Thr His Asn Asp Thr Ser Met Ser His Gly Ala Lys Cys Phe
                500                 505                 510

Ser Ser Asp Phe Met Ala Tyr Asp Ile Ala Cys Asp Arg Trp Ser Val
            515                 520                 525

Leu Pro Arg Pro Asp Ser Thr Met Met Ser Thr Asp Leu Ala Ile Pro
        530                 535                 540

Ala Val Leu His Asn Ser Thr Met Tyr Val Phe Gly Gly Phe Asn Ser
545                 550                 555                 560

Leu Leu Leu Ser Asp Ile Leu Val Phe Thr Ser Glu Gln Cys Asp Ala
                565                 570                 575

His Arg Ser Glu Ala Ala Cys Leu Ala Ala Gly Pro Gly Ile Arg Cys
            580                 585                 590

Val Trp Asn Thr Gly Ser Ser Gln Cys Ile Ser Trp Ala Leu Ala Thr
        595                 600                 605

Asp Glu Gln Glu Glu Lys Leu Lys Ser Glu Cys Phe Ser Lys Arg Thr
        610                 615                 620

Leu Asp His Asp Arg Cys Asp Gln His Thr Asp Cys Tyr Ser Cys Thr
625                 630                 635                 640

Ala Asn Thr Asn Asp Cys His Trp Cys Asn Asp His Cys Val Pro Arg
                645                 650                 655

Asn His Ser Cys Ser Glu Gly Gln Ile Ser Ile Phe Arg Tyr Glu Asn
            660                 665                 670

Cys Pro Lys Asp Asn Pro Met Tyr Tyr Cys Asn Lys Lys Thr Ser Cys
        675                 680                 685

Arg Ser Cys Ala Leu Asp Gln Asn Cys Gln Trp Glu Pro Arg Asn Gln
        690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
                725                 730                 735

Asn Ala Lys Leu Phe Cys Arg Asn His Asn Ala Leu Leu Ala Ser Leu
            740                 745                 750

Thr Thr Gln Lys Lys Val Glu Phe Val Leu Lys Gln Leu Arg Ile Met
            755                 760                 765

Gln Ser Ser Gln Ser Met Ser Lys Leu Thr Leu Thr Pro Trp Val Gly
        770                 775                 780

Leu Arg Lys Ile Asn Val Ser Tyr Trp Cys Trp Glu Asp Met Ser Pro
785                 790                 795                 800

Phe Thr Asn Ser Leu Leu Gln Trp Met Pro Ser Glu Pro Ser Asp Ala
                805                 810                 815
```

```
Gly Phe Cys Gly Ile Leu Ser Glu Pro Ser Thr Arg Gly Leu Lys Ala
            820                 825                 830

Ala Thr Cys Ile Asn Pro Leu Asn Gly Ser Val Cys Glu Arg Pro Ala
            835                 840                 845

Asn His Ser Ala Lys Gln Cys Arg Thr Pro Cys Ala Leu Arg Thr Ala
850                 855                 860

Cys Gly Asp Cys Thr Ser Gly Ser Glu Cys Met Trp Cys Ser Asn
865                 870                 875                 880

Met Lys Gln Cys Val Asp Ser Asn Ala Tyr Val Ala Ser Phe Pro Phe
            885                 890                 895

Gly Gln Cys Met Glu Trp Tyr Thr Met Ser Thr Cys Pro Pro Glu Asn
            900                 905                 910

Cys Ser Gly Tyr Cys Thr Cys Ser His Cys Leu Glu Gln Pro Gly Cys
            915                 920                 925

Gly Trp Cys Thr Asp Pro Ser Asn Thr Gly Lys Gly Lys Cys Ile Glu
            930                 935                 940

Gly Ser Tyr Lys Gly Pro Val Lys Met Pro Ser Gln Ala Pro Thr Gly
945                 950                 955                 960

Asn Phe Tyr Pro Gln Pro Leu Leu Asn Ser Ser Met Cys Leu Glu Asp
            965                 970                 975

Ser Arg Tyr Asn Trp Ser Phe Ile His Cys Pro Ala Cys Gln Cys Asn
            980                 985                 990

Gly His Ser Lys Cys Ile Asn Gln Ser Ile Cys Glu Lys Cys Glu Asn
            995                 1000                1005

Leu Thr Thr Gly Lys His Cys Glu Thr Cys Ile Ser Gly Phe Tyr
    1010                1015                1020

Gly Asp Pro Thr Asn Gly Gly Lys Cys Gln Pro Cys Lys Cys Asn
    1025                1030                1035

Gly His Ala Ser Leu Cys Asn Thr Asn Thr Gly Lys Cys Phe Cys
    1040                1045                1050

Thr Thr Lys Gly Val Lys Gly Asp Glu Cys Gln Leu Cys Glu Val
    1055                1060                1065

Glu Asn Arg Tyr Gln Gly Asn Pro Leu Arg Gly Thr Cys Tyr Tyr
    1070                1075                1080

Thr Leu Leu Ile Asp Tyr Gln Phe Thr Phe Ser Leu Ser Gln Glu
    1085                1090                1095

Asp Asp Arg Tyr Tyr Thr Ala Ile Asn Phe Val Ala Thr Pro Asp
    1100                1105                1110

Glu Gln Asn Arg Asp Leu Asp Met Phe Ile Asn Ala Ser Lys Asn
    1115                1120                1125

Phe Asn Leu Asn Ile Thr Trp Ala Ala Ser Phe Ser Ala Gly Thr
    1130                1135                1140

Gln Ala Gly Glu Glu Met Pro Val Val Ser Lys Thr Asn Ile Lys
    1145                1150                1155

Glu Tyr Lys Asp Ser Phe Ser Asn Glu Lys Phe Asp Phe Arg Asn
    1160                1165                1170

His Pro Asn Ile Thr Phe Val Tyr Val Ser Asn Phe Thr Trp
    1175                1180                1185

Pro Ile Lys Ile Gln Val Gln Thr Glu Gln
    1190                1195

<210> SEQ ID NO 4
<211> LENGTH: 310
<212> TYPE: PRT
```

```
<213> ORGANISM: Homo sapiens

<400> SEQUENCE: 4

Phe Glu Gly Thr Lys Asp Ser Pro Leu Glu His His Leu Tyr Val Val
1               5                   10                  15

Ser Tyr Val Asn Pro Gly Glu Val Thr Arg Leu Thr Asp Arg Gly Tyr
            20                  25                  30

Ser His Ser Cys Cys Ile Ser Gln His Cys Asp Phe Phe Ile Ser Lys
            35                  40                  45

Tyr Ser Asn Gln Lys Asn Pro His Cys Val Ser Leu Tyr Lys Leu Ser
        50                  55                  60

Ser Pro Glu Asp Asp Pro Thr Cys Lys Thr Lys Glu Phe Trp Ala Thr
65                  70                  75                  80

Ile Leu Asp Ser Ala Gly Pro Leu Pro Asp Tyr Thr Pro Pro Glu Ile
                85                  90                  95

Phe Ser Phe Glu Ser Thr Thr Gly Phe Thr Leu Tyr Gly Met Leu Tyr
                100                 105                 110

Lys Pro His Asp Leu Gln Pro Gly Lys Lys Tyr Pro Thr Val Leu Phe
            115                 120                 125

Ile Tyr Gly Gly Pro Gln Gly Gln Ile Glu Ile Asp Asp Gln Val Glu
        130                 135                 140

Gly Leu Gln Tyr Leu Ala Ser Arg Tyr Asp Phe Ile Asp Leu Asp Arg
145                 150                 155                 160

Val Gly Ile His Gly Trp Ser Tyr Gly Gly Tyr Leu Ser Leu Met Ala
                165                 170                 175

Leu Met Gln Arg Ser Asp Ile Phe Arg Val Ala Ile Ala Gly Ala Pro
            180                 185                 190

Val Thr Leu Trp Ile Phe Tyr Asp Thr Gly Tyr Thr Glu Arg Tyr Met
            195                 200                 205

Gly His Pro Asp Gln Asn Glu Gln Gly Tyr Tyr Leu Gly Ser Val Ala
        210                 215                 220

Met Gln Ala Glu Lys Phe Pro Ser Glu Pro Asn Arg Leu Leu Leu Leu
225                 230                 235                 240

His Gly Phe Leu Asp Glu Asn Val His Phe Ala His Thr Ser Ile Leu
                245                 250                 255

Leu Ser Phe Leu Val Arg Ala Gly Lys Pro Tyr Asp Leu Gln Ile Tyr
            260                 265                 270

Pro Gln Glu Arg His Ser Ile Arg Val Pro Glu Ser Gly Glu His Tyr
            275                 280                 285

Glu Leu His Leu Leu His Tyr Leu Gln Glu Asn Leu Gly Ser Arg Ile
        290                 295                 300

Ala Ala Leu Lys Val Ile
305                 310
```